United States Patent [19]

Germer et al.

[11] Patent Number: 6,034,776
[45] Date of Patent: Mar. 7, 2000

[54] MICROROUGHNESS-BLIND OPTICAL SCATTERING INSTRUMENT

[75] Inventors: Thomas A. Germer; Clara C. Asmail, both of Gaithersburg, Md.

[73] Assignee: The United States of America as represented by the Secretary of Commerce, Washington, D.C.

[21] Appl. No.: 09/058,182

[22] Filed: Apr. 10, 1998

Related U.S. Application Data

[60] Provisional application No. 60/043,943, Apr. 16, 1997.

[51] Int. Cl.$^7$ ............................ G01N 21/01; G01N 21/88
[52] U.S. Cl. ....................... 356/369; 356/237.5; 356/446
[58] Field of Search ................................. 356/237, 446, 356/369, 237.4, 237.5

[56] References Cited

U.S. PATENT DOCUMENTS

| | | |
|---|---|---|
| 4,309,110 | 1/1982 | Tumerman ............................. 356/365 |
| 4,376,583 | 3/1983 | Alford et al. . |
| 4,441,124 | 4/1984 | Heebner et al. . |
| 4,668,860 | 5/1987 | Anthon . |
| 4,693,602 | 9/1987 | Wyatt et al. ............................ 356/336 |
| 4,740,708 | 4/1988 | Batchelder . |
| 4,893,932 | 1/1990 | Knollenberg . |
| 4,898,471 | 2/1990 | Stonestrom et al. . |
| 4,991,971 | 2/1991 | Geary et al. ............................. 356/446 |
| 5,032,734 | 7/1991 | Orazio, Jr. et al. . |
| 5,046,847 | 9/1991 | Nakata et al. .......................... 356/237 |
| 5,245,403 | 9/1993 | Kato et al. .............................. 356/369 |
| 5,381,233 | 1/1995 | Chao et al. ............................. 356/369 |
| 5,424,536 | 6/1995 | Moriya ................................... 356/369 |
| 5,479,252 | 12/1995 | Worster et al. . |
| 5,486,919 | 1/1996 | Tsuji ....................................... 356/237 |
| 5,591,985 | 1/1997 | Tsuji ....................................... 356/237 |
| 5,659,390 | 8/1997 | Danko .................................... 356/237 |
| 5,717,485 | 2/1998 | Ito et al. ................................. 356/237 |
| 5,726,455 | 3/1998 | Vurens ................................... 356/369 |
| 5,748,305 | 5/1998 | Shimono et al. ...................... 356/237 |

*Primary Examiner*—Robert H. Kim
*Assistant Examiner*—Zandra V. Smith
*Attorney, Agent, or Firm*—Michael De Angeli

[57] ABSTRACT

A microroughness-blind optical scanner focuses p-polarized light onto the surface of a sample. Scattered light is collected through independently rotatable polarizers by one or more collection systems uniformly distributed over a hemispherical shell centered over the sample. The polarizer associated with each collection system is rotated to cancel the corresponding Jones vector thereby preventing detection of microroughness-scattered light, yielding higher sensitivity to particulate defects. The sample is supported on a positioning system permitting the beam to be scanned over the sample surface of interest.

17 Claims, 3 Drawing Sheets

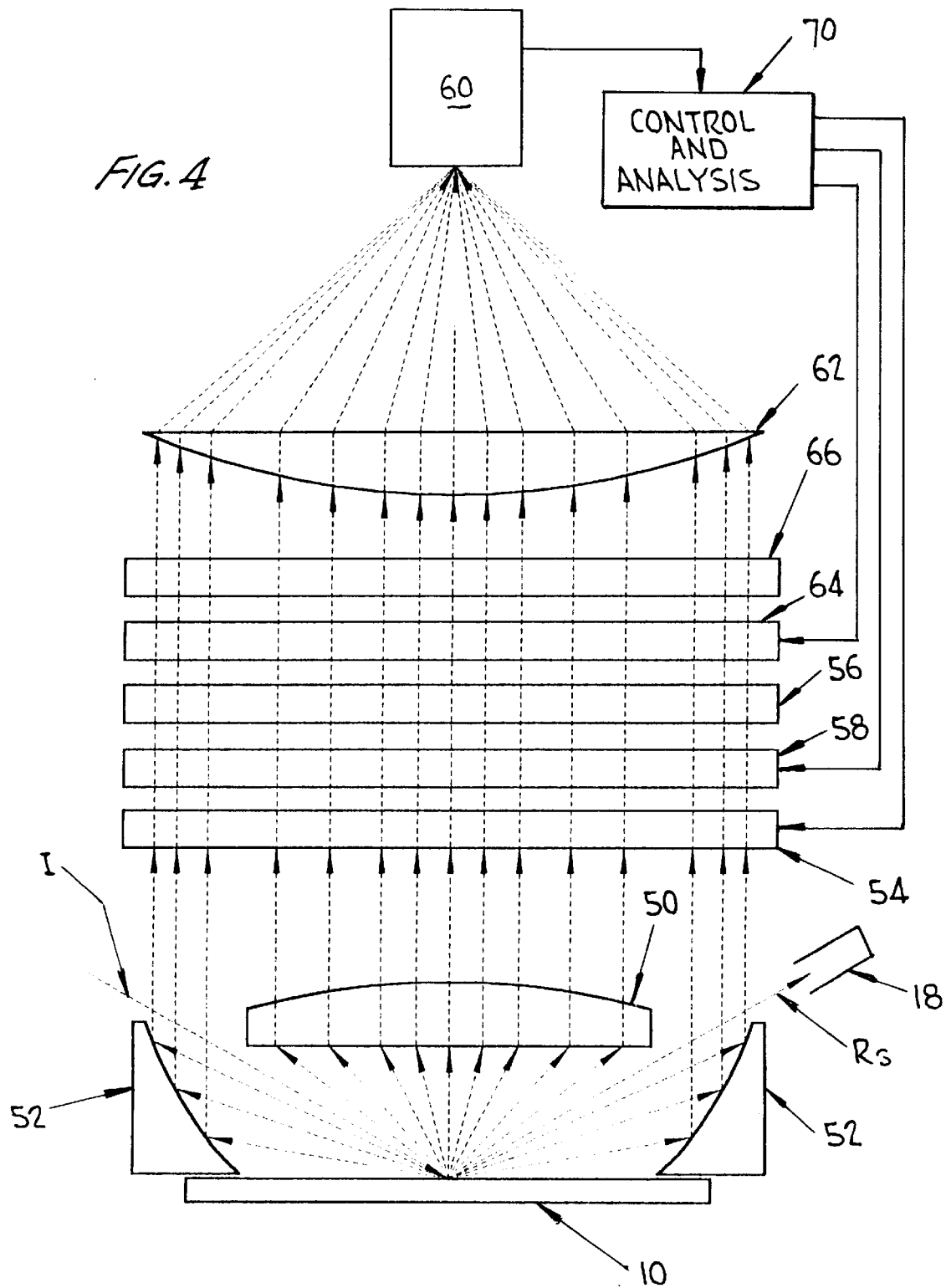

MICROROUGHNESS-BLIND OPTICAL SCATTERING INSTRUMENT

CROSS-REFERENCE TO RELATED APPLICATION

This application claims priority from Provisional Application Ser. No. 60/043,943, filed Apr. 16, 1997.

FIELD OF THE INVENTION

The present invention relates to the detection of particulate contamination on bare silicon wafers and the like. More particularly, the invention relates to an optical scanner insensitive to microroughness yet sensitive to other sources of scatter.

BACKGROUND OF THE INVENTION

Optical scattering techniques are in wide use for inspecting highly polished surfaces, such as those of lenses and silicon wafers as employed as starting materials in semiconductor manufacture. These techniques involve directing a beam of light, typically a focused beam of coherent light from a laser, onto the surface. Most of the beam is "specularly" reflected, that is, is reflected at an angle of reflection equal to the angle of incidence, as from a mirror; however, a small fraction of the beam is "scattered" into other directions. The amount of light scattered is generally representative of the roughness of the surface and the presence of particulates thereon or defects therein, as explained further below.

Optical scattering techniques provide a powerful tool for process monitoring in manufacturing environments because of their noncontact nature and relative ease of use; for example, optical scattering techniques are often employed to detect particulate contamination of silicon wafers on fabrication lines. The requirement that particles smaller than the minimum dimension of the features to be fabricated on the wafer can be reliably detected places strict demands on the sensitivity of an instrument to those particles. One important issue that limits the sensitivity of such an instrument to particulates is scattering from the residual substrate microroughness.

The full strength of the optical scattering technique lies in its ability to diagnose deviations from ideal conditions. For example, optical scattering from smooth surfaces, such as mirrors, transparent optics, and silicon wafers, can yield information about the condition of those surfaces. Surface microroughness, particulate contamination, and subsurface defects result from different adverse conditions in the manufacturing environment; distinguishing between these sources of defects can result in improvements in the ability to identify and correct the sources of such conditions.

Current scanning surface inspection systems (often called wafer scanners) employ optical scattering techniques to detect microroughness, particles, and defects in silicon wafers. Light, usually from a laser, is focused onto the surface of the wafer, and optics (in the form of curved mirrors or lenses) collect light that is scattered by the surface and image it onto a sensitive detector, such as a photomultiplier tube. Generally, as the signal from different points on the sample surface is mapped, one observes localized and non-localized scattering. The localized scattering is attributed to particles and defects, and the non-localized signal is attributed to microroughness. The devices illustrated in U.S. Pat. Nos. 4,376,583 and 4,441,124 are representative of such surface inspection systems.

Some degree of microroughness is always present on a surface, and has the tendency to hide detection of the smallest particles. A particle that is smaller than the wavelength of the scattering light beam scatters light in free space with an efficiency proportional to the sixth power of its diameter. Accordingly, the ability to detect small particles is limited by other sources of optical scatter, such as microroughness. Reduction of the microroughness-induced scatter thus improves the detection of these small particles.

In order to lower the proportion of the total scattering signal due to microroughness, it has been generally recognized that such systems should employ p-polarized light incident at an oblique angle with detection of the scattered light out of the plane of incidence. For example, the system shown by U.S. Pat. No. 4,898,471 employs polarized incident light and collects out-of-plane polarized reflected light but employs only a single detection system with sensitivity to a specific polarization, and does not provide a capability for discriminating roughness from particles at other angles.

To increase the solid angle of collection, conventional scattering systems use a large collection optic; however, as the polarization of the scattered light varies with the scattering angle, a single polarization-selective element only nulls the signal at the center of that optic. For example, U.S. Pat. No. 4,668,860 shows the use of polarization discrimination to distinguish bulk from surface scatter but only collects light in the near-specular direction, and by employing a single polarizer on each of the input and output, fails to recognize that the polarization state varies from one solid angle to the next.

U.S. Pat. No. 4,893,932 employs p- and s- polarized light and assumes that each light of both polarizations is scattered but retains its original polarization. This device uses the difference between two scattered signals to determine the nature of the defect. Although the sample is illuminated at an oblique angle, the invention only collects light scattered normal to the surface.

U.S. Pat. No. 5,032,734 employs the rotational dependence of in-plane scattering to acquire information about the orientation of defects in a material, employing polarization of the incident and detected light only to enhance or diminish the transmission of light into and out of the bulk of the material.

OBJECTS OF THE INVENTION

It is therefore an object of the invention to provide a method and apparatus to discriminate between scatter produced by microroughness and scatter produced by other irregularities on smooth surfaces, so as to allow identification of the source of the defect.

It is a further object of the invention to provide an optical scanning instrument for measuring scattering of light from a surface that is microroughness-blind, so as to be able to provide a signal responsive only to particulates or localized defects.

It is a further object of the invention to provide improved instruments and methods for detecting and identifying small particle contamination on silicon wafers, polished optics, and similar surfaces.

It is yet another object of the present invention to improve the speed and decrease the cost of maintaining a high level of quality control in the manufacture of smooth surfaces.

SUMMARY OF THE INVENTION

The prior art, as discussed above, has operated from an incomplete understanding of the polarization of light scattered by a microrough surface. Consequently the prior art has failed to recognize an important aspect of the present invention, namely, that light scattered due to microroughness can be eliminated from the total scattering signal in every direction, yielding a signal responsive to scattering from particulates and subsurface defects only. Modification of this technique allows measurement of microroughness. Advances in the interpretation of scattered light enable optical scattering techniques to be employed to support new and vastly superior quality control applications.

According to the invention, focused p-polarized light is scanned across the surface of a sample and collected by polarization-sensitive collection systems distributed substantially uniformly over a hemispherical shell centered over the sample. In a first embodiment, polarizers associated with each of a number of individual collection systems are independently rotatable to cancel the signal from microroughness, thereby preventing detection by that system of microroughness-scattered light. In a second embodiment, one or more spatial light modulators are used in combination with a polarizer to control the incidence of scattered light on a single detector.

In either embodiment, the instrument of the invention collects light over a large solid angle, with the light scattered into each direction within that solid angle being individually discriminated to pass only light polarized orthogonal to that scattered by microroughness.

BRIEF DESCRIPTION OF THE DRAWINGS

FIG. 3 is a diagram of a single collection system.

FIG. 4 is a diagram of the collection system of a second embodiment of the invention.

DESCRIPTION OF THE PREFERRED EMBODIMENTS

Figure 1:
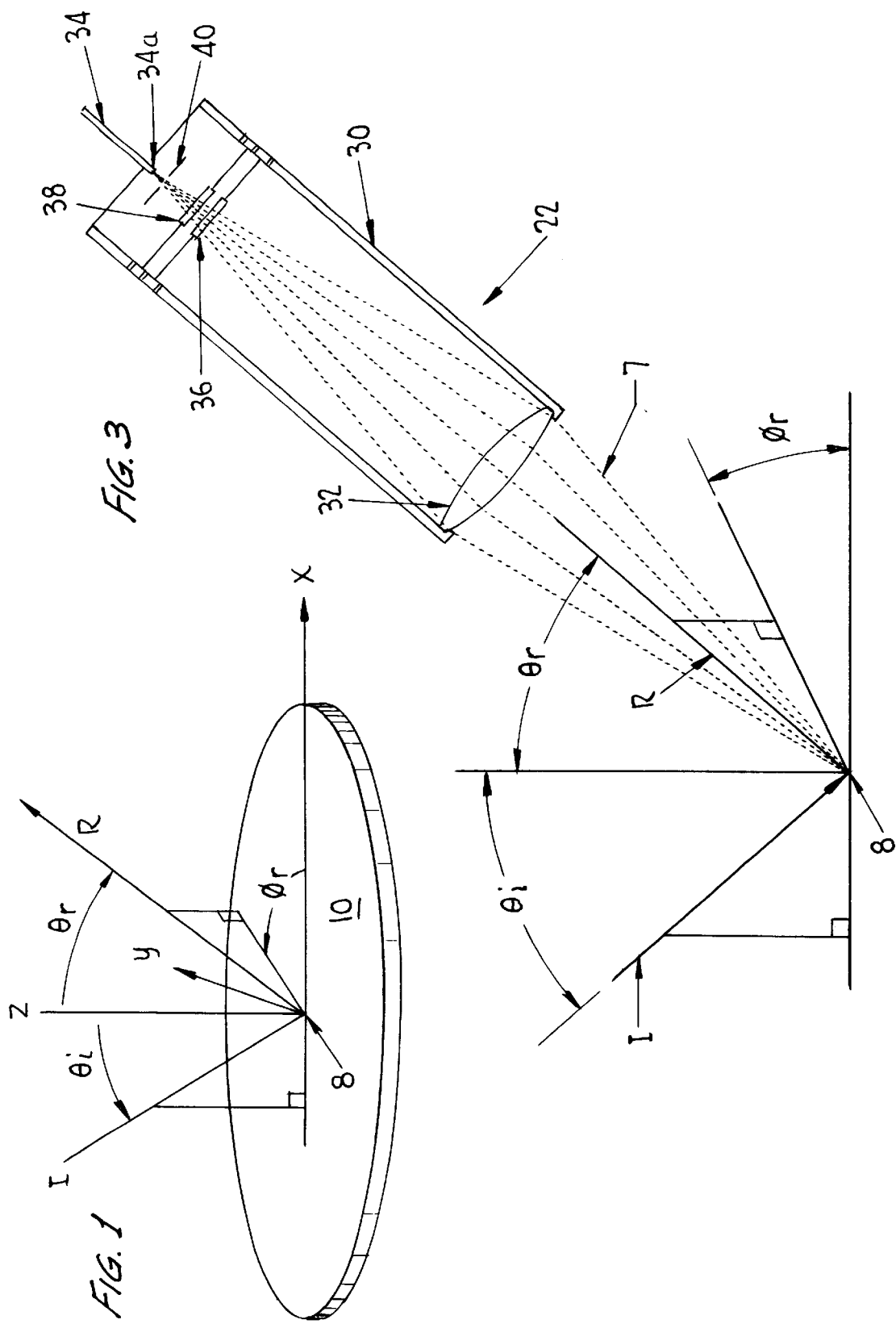
FIG. 1 is a diagram showing the reference system employed herein to define optical geometry.

In order to describe the invention, it is necessary to review the theory of optical scattering from microrough surfaces. As shown in FIG. 1, an incident beam I of coherent light with wavelength $\lambda$ is incident onto a point 8 on surface 10 of a material having a dielectric function $\in$ (evaluated at $\lambda$) at an angle of incidence $\theta_i$. Most of the incident beam I is specularly reflected through an angle of reflection equal to $\theta_i$, forming a reflected beam in the same plane as I. However, a fraction of the incident beam I is scattered in many directions. The scattered beams are denominated R, and their direction parameterized by polar angle $\theta_r$ and azimuthal (out-of-plane) angle $\phi_r$.

The polarization states of the incident and scattered light can be defined with respect to the planes of incidence and scatter as follows. Considering the planes of incidence and scatter as being defined by a line normal to the sample and the incident and scatter directions, respectively, the electric field lies within the respective plane when the beam is p-polarized and perpendicular to that plane when it is s-polarized. (It will be appreciated that "p-polarized" as used herein is equivalent to "transverse magnetic" or "TM"; similarly, "s-polarized" is equivalent to "transverse electric" or "TE"). The power spectral density (PSD) of the surface height function is given by S(f), where $f=f_x\hat{x}+f_y\hat{y}$ is a two-dimensional spatial frequency in the plane of the surface (defined by the unit vectors $\hat{x}$ and $\hat{y}$). Then, according to the results of first-order vector perturbation theory, the bidirectional reflectance distribution function (BRDF), defined as the scattered radiance normalized by the incident irradiance, is given by $$BRDF = \frac{16\pi^2}{\lambda^4}\cos\theta_i\cos\theta_r S(f) \times \sum_{jk}|q_{jk}e_j e_k|^2$$

where the dimensional spatial frequency vector f is related to $\theta_i$, $\theta_r$, and $\phi_r$ by the Bragg relations $\lambda f_x = \sin\theta_r \cos\phi_r - \sin\theta_i$ $\lambda f_y = \sin\theta_r \sin\phi_r$.

The $e_j$ and $e_k$ are the elements of the unit Jones vectors, that is, vectors defining the relative amplitudes of the incident and scattered electric fields (in the s-p basis), respectively, and the $q_{jk}$ are given by $$q_{ss} = \frac{(\epsilon-1)\cos\phi_r}{\left(\cos\theta_i + \sqrt{\epsilon-\sin^2\theta_i}\right)\left(\cos\theta_r + \sqrt{\epsilon-\sin^2\theta_r}\right)}$$

$$q_{sp} = \frac{-(\epsilon-1)\sin\phi_r\sqrt{\epsilon-\sin^2\theta_r}}{\left(\cos\theta_i + \sqrt{\epsilon-\sin^2\theta_i}\right)\left(\epsilon\cos\theta_r + \sqrt{\epsilon-\sin^2\theta_r}\right)}$$

$$q_{ps} = \frac{-(\epsilon-1)\sin\phi_r\sqrt{\epsilon\sin^2\theta_i}}{\left(\epsilon\cos\theta_i + \sqrt{\epsilon-\sin^2\theta_i}\right)\left(\cos\theta_r + \sqrt{\epsilon-\sin^2\theta_r}\right)}$$

$$q_{pp} = \frac{-(\epsilon-1)\left(\sqrt{\epsilon-\sin^2\theta_i}\sqrt{\epsilon-\sin^2\theta_r}\cos\phi_r - \epsilon\sin\theta_i\sin\theta_r\right)}{\left(\epsilon\cos\theta_i + \sqrt{\epsilon-\sin^2\theta_i}\right)\left(\epsilon\cos\theta_r + \sqrt{\epsilon-\sin^2\theta_r}\right)}.$$

The coordinate systems for the incident and scattered light are such that each respective set of vectors $\{\hat{s}, \hat{p}, \hat{k}\}$ define right-handed coordinate systems, where $\hat{k}$ is in the direction of propagation of the light. The out-of-plane angle $\phi_r$ is measured in a right-handed sense about the out-of-the-surface normal.

The present invention exploits the knowledge of the Jones matrix $q_{jk}$ given above. The p→p scattering data from surface microroughness vanishes for certain out-of-plane angles. These angles are bidirectional equivalents of Brewster's angle, where the induced dipole moment in the material is perpendicular to the plane of scatter. The usefulness of this behavior is that scattering mechanisms other than microroughness, that is, resulting in signal contributions that would otherwise be masked by residual microroughness, can be detected.

Polarized light scattering measurements reported by the inventors at "Bidirectional Ellipsometry and its Application to the Characterization of Surfaces", *SPIE* Vol. 3121, pp. 173–182 (1997) show that for a fixed incident direction, incident polarization state, and scattering direction, the scattered light is nearly polarized linearly, although at an angle that is tilted with respect to the p or the s axis. Although the scattering is not strictly p or s polarized, the fact that it is well defined and follows the prediction of the model allows one to make a microroughness-blind scattering instrument that integrates over a large portion of the entire hemisphere, by appropriately choosing the detected polarization state for each corresponding scattering direction. (Note that the Jones matrix is a function of the optical constant of the sample, so that the polarization will also depend upon the material under test.)

Stated differently, as different scattering sources, such as microroughness, subsurface defects, and particulate contamination, have different effects on the polarization, polarization-sensitive detection performed according to the invention permits discrimination between the different sources of scatter; an instrument can thus be made to be, for example, microroughness-blind, so that the total detected signal is due to particulates and subsurface defects. (It should also be appreciated that in some cases, light of other than p-polarization may be usefully employed as the incident beam; for example, circularly polarized light has been found to improve the uniformity of detection for scattering from defects within a dielectric layer.) Although the absolute magnitude of the bidirectional reflectance distribution function has proved to be useful for analyzing scattered light, this magnitude is not so sensitive to the microscopic sources of scatter as to the correlations between them. In contrast, the polarization of scattered light strongly indicates the paths that light follows during its trajectory and therefore is more sensitive to the microscopic details of the scattering process.

Measurements have been made which verify the accuracy of the model. See "Polarization of Out-of-Plane Scattering from Microrough Silicon", Germer et al, *Optics Letters*, Vol. 22, No. 17, pp. 1284–1286, Sep. 1, 1997. The work reported there shows that the polarization of light scattered into any direction is deterministic and matches the predictions of the model. Other models have been developed for scattering from other sources, namely particulate contamination and subsurface defects, and the polarizations predicted by these other scattering sources are sufficiently distinct to allow a discrimination to be made between the different scattering mechanisms when the incident light is p-polarized and at an oblique angle of incidence ($\theta_i \neq 0$). See Germer, "Angular dependence and polarization of out-of-plane optical scattering from particulate contamination, subsurface defects, and surface microroughness", *Applied Optics*, Vol. 36, No. 33, pp. 8798–8805 (Nov. 20, 1997).

Figure 2:
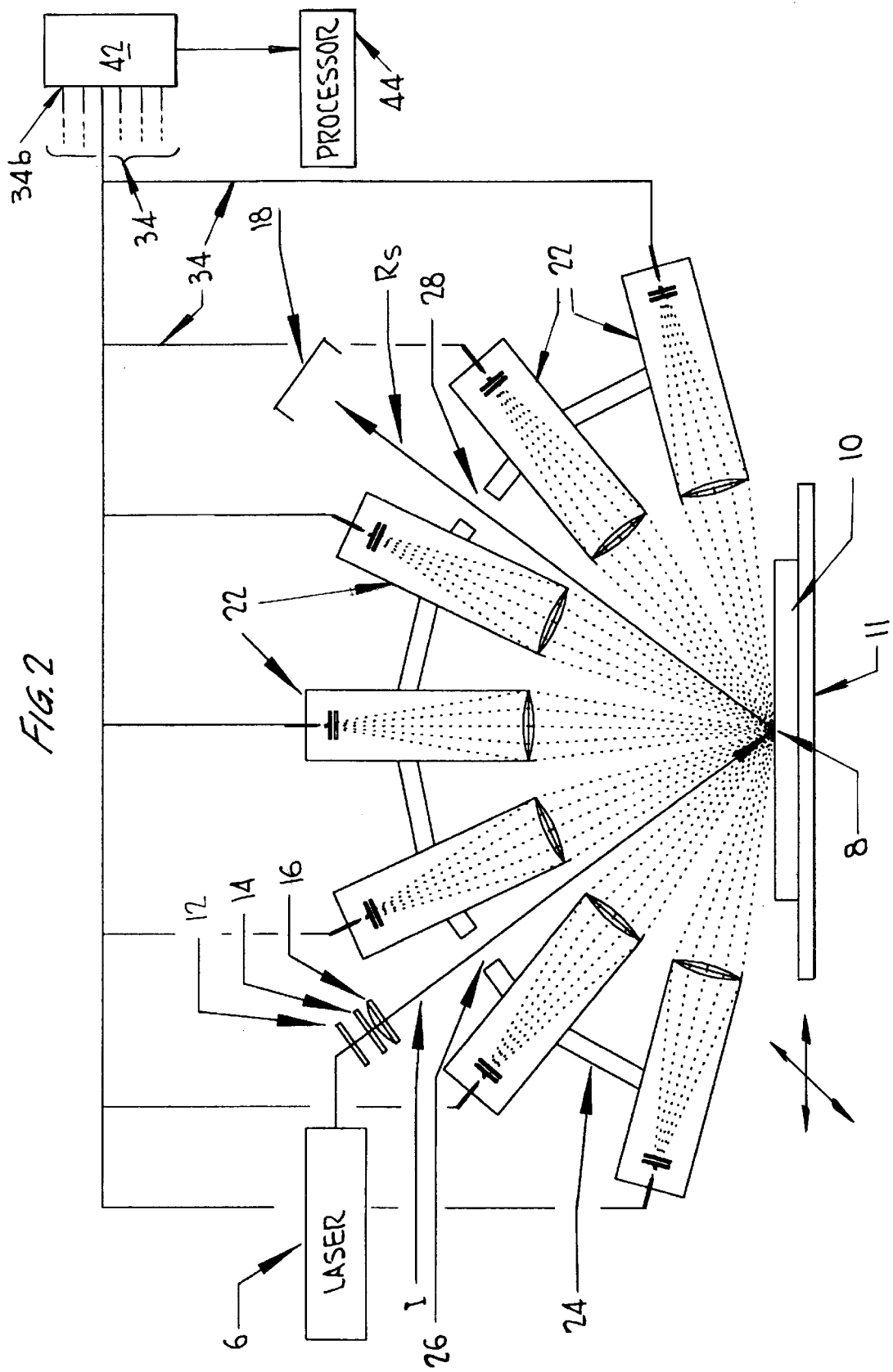
FIG. 2 is a schematic diagram illustrating the overall design of a first embodiment of the instrument of the invention, including plural collection systems. The collection systems are only shown in a single plane; however, it is to be understood that such collection systems substantially cover the hemisphere over the surface to be inspected.

A first embodiment of an instrument for implementing the invention is shown in FIG. 2. A coherent source of light, for example laser 6, produces a beam of monochromatic incident light I onto a region 8 on sample 10 at some incident angle $\theta_i$. The sample lies upon a positioning system 11 which allows the entire sample to be scanned by the laser beam. The polarization state of the incident light is controlled with an optional polarizer 12 and an optional linear retarder (half-wave plate) 14 so as to be p-polarized when incident onto the sample 10. The light is focused onto the sample 10 using lens 16. The specularly reflected beam $R_s$ is directed into an efficient beam dump 18 to eliminate stray light. Situated about the region where incident beam I strikes sample 10 are a plurality of collection systems 22. These systems are held in place by a hemispherical shell 24. Collection systems 22 are disposed so as to cover as much of the scattering hemisphere as possible, but there exists space for an entrance port 26 to allow the incident light I to be focused on the sample and an exit port 28 to permit the specularly reflected beam $R_s$ to escape. Positioning system 11 translates and/or rotates sample 10 in order to successively bring the focus of incident light I onto each portion of its surface.

Each collection system 22 is housed in a tube 30 as shown in FIG. 3. A lens 32 focuses the scattered light R from the illuminated region 8 of the sample onto the distal end 34a of an optical fiber 34. A quarter wave plate 36, provided to convert elliptically polarized light into linearly polarized light, and a polarizer 38, to discriminate between various polarization states, are disposed between the illuminated region 8 on the sample and the end 34a of optical fiber 34. By placing the quarter wave plate and the polarizer close to the optical fiber, the size of these elements can be kept small, reducing costs. The quarter wave plate and the polarizer can be independently rotated. Since the light scattered in some directions may be linearly polarized, the quarter wave plate is optional on some of the collection systems. The size of the optical fiber defines the field of view at the sample. The magnification of the lens and the position of the optical fiber are such that the image of the focused region on the sample is focussed on and underfills the end 34a of the optical fiber.

In the embodiment shown, the proximal ends 34b of the optical fibers 34 from each collection system are juxtaposed to a single detector 42, shown in FIG. 2, such as a photomultiplier tube, effectively summing the total scattered signal. The signal from detector 42 is transmitted to a processor 44 for correlation with calibrated values to characterize the condition of the sample surface. Alternatively, individual detectors can be disposed in the positions of the distal ends 34a of optical fibers 34, in which case field-of-view apertures 40 may be required. In this embodiment, the signals provided by each of the detectors may be summed electronically to yield a value for the total scattering, or may be processed individually, for reasons discussed below. similarly, individual detectors may be juxtaposed to the proximal ends 34b of the fiber optics 34.

Further modifications of this embodiment of the invention include use of detectors that are intrinsically polarization sensitive, in lieu of combinations of detectors and polarizers; employment of electro-optic devices in lieu of the polarizers and/or waveplates, as discussed below in connection with FIG. 4; and disposition of the polarizers and waveplates before the collection lens, rather than after. In this latter alternative, a non-imaging light collector could be used, eliminating the lens.

Each collection system will have an associated center scatter direction parameterized by $\theta_s$ and $\phi_s$. Where the instrument is to be operated in a microroughness-blind manner, that is, to measure particulates and surface defects, the waveplate and polarizer are rotated to a desired orientation in a calibration operation described below, so that light scattered by microroughness will not be detected.

Each collection system 22 of the instrument of the invention is aligned using two test samples. During alignment, it is helpful to disconnect all the optical fibers from the detector, except that of the collection system 22 which is then being adjusted.

First, a highly scattering sample is used to align the optical fibers to their respective focus points. The sample should be the same thickness as a real sample, so that the focus is not shifted in position. The use of a highly scattering sample simply makes alignment simpler. If the sample is also depolarizing, then the waveplate 36 and polarizer 38 do not need to be positioned for this step. If the sample is not depolarizing, then the waveplate and polarizer will need to be positioned in a way that will allow at least some of the light to pass through.

Once all of the fibers are aligned, then a new sample should be placed into the sample position in order to align the polarization elements. This sample should be known to scatter due to microroughness, and be of the same material as that which will eventually be used with the instrument.

Such samples are available commercially for the calibration of microroughness instrumentation. The polarizer 38 and quarter wave plate 36 are then rotated to minimize the signal.

In typical use, the light from all of the optical fibers is combined to yield a single value indicative of the total scattering due to particulates and subsurface defects. The optical fibers can be used to transport the individually-collected signal to a single detector as described above; alternatively, the light collected by each collection system can be converted to an electrical signal by an individual detector, and these signals electronically combined to yield a single signal. The latter arrangement allows the signals from each collection system to be electronically or optically multiplexed, such that the distribution of scattered light can be analyzed, e.g., by processor 44, to reveal further information, such as the size, shape, or material of a defect.

It is beneficial to employ as many individual collection systems as possible, thus reducing the solid angle "seen" by each; by doing so, the total system will better discriminate against surface microroughness, since the polarization due to microroughness will vary over any finite solid angle. For a finite solid angle, the discrimination is limited by the changing polarization state over that solid angle.

Since it is often desirable to measure the microroughness of a wafer, this entire system can alternatively be made microroughness-sensitive rather than insensitive by simply rotating the input polarization (e.g., with a λ/2 waveplate 14 or polarizer 12 shown in FIG. 2) so that the incident light becomes s-polarized. An electro-optic modulator (see discussion of FIG. 4 below) could be employed for the same purpose.

The uniqueness of the above-described invention is that scattered light is collected over a very large solid angle, ideally the entire hemisphere over the sample. However, unlike a total integrated scatter configuration (i.e., using a single detector), the signal resulting from surface microroughness is not increased, since it is everywhere nulled. The effect is to improve the signal-to- (microroughness-induced) noise ratio of the signal due to scattering from particulates and surface defects. This invention, therefore, substantially lowers the detectable size for particles on microrough surfaces.

It will be appreciated that insofar as the instrument of the invention detects the amount of light reaching the detector after passing through a polarizer between the sample and the detector, each detector effectively measures the polarization of the light reaching the collection system. Further, it will be recognized that correlation of the polarization of the light reaching each detector with respect to the detector's position in the hemisphere over the region of the sample from which the scattering takes place can be used to determine the actual source of scattered light, that is, other than from microroughness. A signature analysis of the relative intensity signals from each detector may indicate the type of defect or particle, and the absolute intensity may provide information about the size of the defect or particle.

As noted, the optical fibers of the embodiment shown can be replaced with individual detectors. In this variation, the signals from each of the detectors are individually buffered or amplified before being summed together with the signals from the other collection systems. This embodiment of the invention would yield a higher noise level if the detectors are not capable of counting individual photons. However, for some applications, such as the evaluation of lower quality optics, this loss of signal-to-noise ratio may be tolerated.

FIG. 4 shows a cross-sectional view through a portion of a second embodiment of the instrument of the invention. As previously, an incident beam I is directed onto the surface of a sample 10. Most of the incident beam is specularly reflected as $R_s$, and is collected in a beam dump 18. However, some fraction of the incident light is scattered from the surface.

In this embodiment, the scattered light is collected by a lens 50; a circular curved mirror 52 may be provided to increase the collection solid angle. A spatial light modulator ("SLM") 54 followed by a polarizer 56 are disposed at the back focal plane of lens 50 and mirror 52. Such SLMs are well-known in the art, and comprise panels divided into a large number of picture elements, or "pixels"; the SLM is electronically-controlled such that each pixel has an adjustable retardance. When used in combination with a linear polarizer, an SLM may be controlled electronically to select the linear polarization state of light passing through both the SLM and the polarizer on a pixel by pixel basis; when two SLMs are used in conjunction with a linear polarizer, light of any elliptical polarization state may be electronically selected to pass through the two SLMs and the polarizer. Accordingly, light incident on specific areas of the SLM and polarizer is transmitted therethrough, or absorbed, depending on the state of the pixels thereof. As used in this embodiment of the invention, each pixel will correspond to a specific scattering direction. (As indicated above, SLMs or other electro-optic devices could also be employed in the embodiment of FIGS. 2 and 3.) SLM 54 and polarizer 56 are aligned so that as each pixel (or group of pixels) of SLM 54 is appropriately electronically controlled, only light of a particular polarization state passes through polarizer 56. In many cases, a second SLM 58 will be required in order to cancel light of elliptical polarization state. The light passing through this polarization-sensitive optical system is then collected and measured by a detector 60; detector 60 may comprise an imaging detector, requiring lens 62, or a non-imaging detector, and may comprise a single detector or an array of detectors.

An array of detectors may be provided either at the back focal plane, in place of lens 62, or at the image plane of lens 62. In the latter case, the instrument would be operated as a microscope, observing different locations on the sample 10, while being insensitive to microroughness. In the former case, the array of detectors could be operated to describe the angular dependence of the scattered light, thus allowing analysis to determine the causes of the scattering.

Reflection of the scattered light from mirror 52 in the system shown will cause some retardation of the light; second SLM 58 will be required to compensate for this effect. SLM 58 will also be required in systems measuring light scattered from samples including dielectric films or metallic samples, which introduce elliptical polarization.

A further enhancement includes a third SLM 64 followed by a second polarizer 66. This feature allows specific "channels" to be turned on or off, by control of SLM 64, allowing the light scattered in various directions to be separately measured. This feature would also allow improvement in detection of defects on patterned surfaces, where bright diffraction peaks resulting from the pattern must be removed from the scattering signal.

It will be appreciated that this embodiment of the instrument of the invention includes a single collection system. The system comprising SLMs 54 and 58 and polarizer 56 is capable of measuring the polarization of light scattered from the surface, that is, of determining the total amount of light of a given polarization scattered from the surface; if the additional SLM 64 and polarizer 66 are provided, the scattered light can be measured as a function of the direction of scattering. Control of the SLMs by a computer device 70, and analysis thereby of the polarization of the scattered light as a function of the direction of scattering, are considered to be within the skill of the art given the disclosure hereof.

It should be appreciated that the lens 50 and mirror 52 might desirably be replaced with a more complex optical system. For example, lens 50 could be replaced with a multiple-element system, to minimize spherical aberration, or could be configured as a microscope objective. The curved mirror 52 could be replaced with transmissive optics to transport light to the back focal plane for detection.

The system of FIG. 4 has several advantages over that of FIGS. 2 and 3. In particular, although the cost of the SLMs is currently high, the capability provided for electronically varying each element's polarization direction allows ready "tuning" of the system, in order to analyze the polarization of scattering from specific defects, increase the number of effective collection directions, and vary the "blindness" from point to point on a semiconductor wafer. The latter capability would be particularly useful during the inspection of patterned materials, since different regions of the sample will have differing optical properties.

While several preferred embodiments of the invention have been described in detail, these are exemplary only, and should not be considered to limit the invention. The invention is to be limited only by the following claims.

What is claimed is:

1. An apparatus for differentiating between sources of light scattering from the surface of a sample, comprising:
    means for supporting and positioning the sample;
    means for generating a monochromatic beam of polarized light;
    means for directing said beam of light onto a region of interest on the sample surface incident at an oblique angle thereto, such that said light is scattered in a plurality of directions;
    a collection system for simultaneously receiving light from said beam after scattering from said sample surface region in said plurality of directions, said collection system comprising means for independently measuring the full polarization state of the scattered light received by said collection system from each direction of scattering; and
    processing means for correlating characteristics of said scattered light with characteristics of said sample surface region; and
    wherein said means for independently measuring the full polarization state of the scattered light received by said collection system comprises a polarizer to filter out light scattered by a selected scatter mechanism.

2. The apparatus of claim 1, further comprising means for measuring the amount of scattered light of a particular polarization as a function of the direction of scattering.

3. The apparatus of claim 1 wherein said beam of light is p-polarized.

4. The apparatus of claim 1 wherein said means for supporting and positioning the sample successively positions each region of interest on the sample surface under the focus of said beam of light to permit mapping of the sample surface.

5. An apparatus for differentiating between sources of light scattering from the surface of a sample, comprising:
    means for supporting and positioning the sample;
    means for generating a monochromatic beam of polarized light;
    means for directing said beam of light onto a region of interest on the sample surface incident at an oblique angle thereto, such that said light is scattered in a plurality of directions;
    a collection system for simultaneously receiving light from said beam after scattering from said sample surface region in said plurality of directions, said collection system comprising means for measuring the polarization of the scattered light received by said collection system from each direction of scattering, wherein said collection system for receiving light from said beam after scattering comprises a plurality of collection systems mounted on a hemispherical support frame having said region at the origin; and
    processing means for correlating characteristics of said scattered light with characteristics of said sample surface region;
    wherein each of said plurality of collection systems comprises a detector, a selectively rotatable polarizer positioned between said detector and said sample surface region and a lens to focus said received light through said polarizer onto said detector.

6. The apparatus of claim 5, wherein said support frame is a shell having an entrance port for receiving said incident beam of light and an exit port for permitting the exit of specularly reflected light.

7. The apparatus of claim 5, wherein said processing means for correlating characteristics of said scattered light with characteristics of said sample surface region is separately responsive to signals provided by the detector of each said collection system.

8. The apparatus of claim 5, further comprising a selectively rotatable quarter wave plate positioned between said polarizer and said sample surface region.

9. The apparatus of claim 5, further comprising a field-of-view aperture positioned between said lens and said detector.

10. The apparatus of claim 8, wherein each of said plurality of collection systems further comprises at least one optical fiber disposed between the combination of said lens and said selectively rotatable polarizer and a remote detector for transmitting said reflected scattered light to said remote detector for processing.

11. The apparatus of claim 10, wherein second ends of said optical fibers of each of said collection systems are juxtaposed to a single detector for providing a single output signal responsive to light collected by all of said collection systems.

12. The apparatus of claim 10, further comprising a selectively rotatable quarter wave plate positioned between said polarizer and said sample surface region.

13. An apparatus for differentiating between sources of light scattering from the surface of a sample, comprising:
    means for supporting and positioning the sample;
    means for generating a monochromatic beam of polarized light;
    means for directing said beam of light onto a region of interest on the sample surface incident at an oblique angle thereto, such that said light is scattered in a plurality of directions;
    a collection system for simultaneously receiving light from said beam after scattering from said sample surface region in said plurality of directions, said collection system comprising means for independently measuring the full polarization state of the scattered light received by said collection system from each direction of scattering; and
    processing means for correlating characteristics of said scattered light with characteristics of said sample surface region;

wherein said collection system for receiving light from said beam after scattering comprises at least one electronically-controlled spatial light modulator, said at least one spatial light modulator comprising at least one pixel having independently adjustable retardance and being arranged such that light scattered from said sample surface region is incident thereon, a polarizer, and a detector for measuring the amount of light passing through said spatial light modulator and said polarizer.

14. The apparatus of claim 13, further comprising an additional electronically-controlled spatial light modulator and a second polarizer, and means for determining the polarization of light scattered from said sample surface region as a function of the direction of scattering.

15. A method of optically scanning a surface, comprising the steps of:

(a) focusing a polarized beam of monochromatic light on a region of interest on the surface at an oblique angle of incidence, such that light is scattered in a plurality of directions:

(b) collecting the scattered light by a collection system extending over the hemisphere surrounding said region, said collection system comprising detection means for providing signals responsive to the intensity of scattered light incident thereon and one or more polarizers between said detection means and said region, said polarizer(s) having been aligned such that said detection means produces a null output signal responsive to light scattered due to microroughness, wherein said collection system comprises a plurality of individual detection means, each comprising an optical fiber having a distal end positioned to collect light scattered from said surface region and a proximal end juxtaposed to an optical detectors;

(c) detecting and processing said signal to produce a microroughness-blind characterization of said region; and (d) repeating steps (a)–(c) with respect to each region of interest on said surface.

16. The method of claim 5, wherein the proximal ends of each of said optical fibers are juxtaposed to a single optical detector.

17. The method of claim 5, wherein said detection means comprises an optical detector disposed to directly measure the intensity of light of a particular polarization scattered from said region, and said method comprises the further step of separately analyzing the signals provided by each of said detectors as a function of the direction of scattering.

* * * * *